United States Patent [19]
Engelbrecht et al.

[11] Patent Number: 4,906,446
[45] Date of Patent: Mar. 6, 1990

[54] FILLER FOR DENTAL MATERIALS AND DENTAL MATERIALS CONTAINING THE SAME

[76] Inventors: Jürgen Engelbrecht, Petkumstrasse 18, D-2000 Hamburg 76; Michael Günther, Edvard-Much-Str. 39, D-2000 Hamburg 74; Helmut von Wallis, Hirschberger Strasse 2, 2359 Henstedt-Ulzburg 2, all of Fed. Rep. of Germany

[21] Appl. No.: 162,240

[22] Filed: Feb. 29, 1988

Related U.S. Application Data

[63] Continuation of Ser. No. 660,324, Oct. 12, 1984, abandoned, which is a continuation-in-part of Ser. No. 568,268, Jan. 4, 1984, abandoned.

[30] Foreign Application Priority Data

Jul. 1, 1983 [DE] Fed. Rep. of Germany ....... 3300321

[51] Int. Cl.$^4$ .............................................. C01B 33/12
[52] U.S. Cl. .................................... 423/335; 423/338; 423/339; 523/104; 524/493
[58] Field of Search ....................... 423/335, 338, 339; 523/109; 524/493

[56] References Cited

U.S. PATENT DOCUMENTS

| | | | |
|---|---|---|---|
| 3,935,299 | 1/1976 | Kiselev et al. | 423/339 |
| 4,032,504 | 6/1977 | Lee, Jr. et al. | 106/288 B |
| 4,036,923 | 7/1977 | Laufer et al. | 423/335 |
| 4,217,264 | 8/1980 | Mabie et al. | 106/288 B |
| 4,306,913 | 12/1981 | Mabie et al. | 106/288 B |
| 4,388,069 | 7/1983 | Orlowski | 423/228 |

FOREIGN PATENT DOCUMENTS

| | | |
|---|---|---|
| 2446546 | 4/1975 | Fed. Rep. of Germany . |
| 2462271 | 9/1976 | Fed. Rep. of Germany . |
| 866326 | 4/1961 | United Kingdom . |

OTHER PUBLICATIONS

*Concise Chemical and Technical Dictionary*, H. Bennett, ed., Chemical Publishing Co., Inc., N.Y., N.Y., 1974, p. 939.

Primary Examiner—Joseph L. Schofer
Assistant Examiner—Bernard Lipman
Attorney, Agent, or Firm—Keil & Weinkauf

[57] ABSTRACT

Silica gels of a mean grain size of about 0.5 to 50 $\mu$m are subjected to a heat or acid treatment that considerably reduces their surface area and the volume of pores smaller than 50 nm, while maintaining approximately the same grain size distribution and amorphous structure. These products are colorless and can be worked into a resinous molding material in relatively large quantities, especially as a filler for dental materials based on polymerizable monomers, in particular mono-, di- or polyfunctional esters of acrylic or methacrylic acid. In the completely hardened condition, these materials have good mechanical characteristics, less polymerization shrinkage, very low thermal expansion coefficients, excellent transparency and tooth similarity resulting from the favorable refractive index of the filler, as well as very good ability to be polished and abrasion resistance.

15 Claims, No Drawings

FILLER FOR DENTAL MATERIALS AND DENTAL MATERIALS CONTAINING THE SAME

This application is a continuation of application Ser. No. 660,324, filed on Oct. 12, 1984, now abandoned, which application is a continuation-in-part of application Ser. No. 568,268 filed Jan. 4, 1984 and now abandoned.

This invention relates to a surface area-reduced silica gel as a filler for dental materials and dental materials containing the same.

In addition to one or several polymerizable monomers, polymerization catalysts, accelerators, UV-stabilizers, etc., dental materials based on polymerizable compounds contain, as a rule, an inorganic filler. The inorganic filler is added for the purpose of decreasing polymerization shrinkage, lowering the thermal expansion coefficient, reducing water absorption, and increasing the hardness of the obtained polymers, so-called "composites".

Inorganic fillers may be members of the group of so-called "macrofillers", i.e. fillers with a particle diameter of 0.1 to 100 μm. Examples of macrofillers are ground quartz, quartz or silica glasses, aluminum oxide, ceramic or mineral fillers. These types of substances can be worked into dental materials in relatively large quantities. In composite materials, for example, they may constitute about 60 to 80 percent by weight of the overall composition. The higher the percentage of inorganic filler, the better the physical characteristics of the materials obtained by polymerization, such as low expansion coefficients, low water absorption, and high color stability. However, the higher the percentage of macrofillers used, the more difficult it is to polish the synthetic materials obtained by polymerization.

The surface roughness of the synthetic composite materials causes problems, as it promotes the deposit of plaque which, in turn, can cause discoloration and marginal secondary caries.

Another disadvantage of the above composite dental materials is their low abrasion resistance. Because of their unsatisfactory abrasion resistance, materials containing inorganic macrofillers cannot be used for filling molars where, despite the toxicological risk of mercury, amalgam fillings are still predominantly used.

In order to improve the polishability and abrasion resistance of synthetic substances of this type, it has been suggested, among other things, to use fillers with minimum primary particle sizes, so-called "microfillers", in dental materials.

From Hirasawa (Reports of the Institute for Medical and Dental Engineering 2, 55–61, 1968) and from DE-OS 2 403 211, it is known that preparing dental materials using amorphous silicic acids, such as silica gel or pyrogenic silicic acid, having primary particle sizes of 5–50 μm, results in highly polishable molding substances with good abrasion resistance characteristics after hardening. However, this improvement in polishability and abrasion resistance is achieved at the expense of other important characteristics; for example, there is increased water absorption and lower color stability. High water absorption and low color stability are caused by the resins contained in the dental materials. It is therefore endeavored to reduce the proportion of resin and to eliminate these undesirable characteristics by increasing the percentage of inorganic fillers. Solving this problem by using the so-called "microfillers" is unsatisfactory because they can only be worked into a dental paste materials in quantities of up to about 50 percent by weight.

In addition, when using microfillers, a fairly high thermal expansion coefficient must be accepted. When the filler material and the substance of the tooth have a thermal expansion coefficient that is very different, the change of temperature occurring, for example, during eating, causes the so-called "pump effect". With deep cavities the resulting marginal gap may admit bacteria and cause secondary caries or damage to the pulp.

It has been attempted to avoid these disadvantages by agglomerating very small particles of pyrogenic and precipitated silicic acid, in the millimicron size range, predominantly with oxidic binding agents, to form much larger particles in the micron range. In this agglomerated form, they are used as fillers in dental materials, as described in WO 81/01366. Pastes may have higher contents of these fillers than of normal "microfillers". The resulting molding substances can be polished and exhibit satisfactory abrasion resistance.

Undoubtedly, this development represents an improvement. However, in comparison to what can be achieved in the case of "macrofillers", the molding substances are far below what is required with respect to coefficients of thermal expansion.

It is therefore the objective of the invention to provide a new filler that, with all its characteristics, is within the ranges that formerly were only achieved by using "macrofillers", but also, has excellent polishability and abrasion resistance characteristics.

According to the invention, this objective is achieved by the use of a surface area-reduced silica gel, which has been prepared by roasting a silica gel of a mean grain size of about 0.5 to 50 μm at a temperature between 500° and 1,200° C. or/and by acid-catalytically treating a silica gel, and which has an essentially unchanged mean grain size of about 0.5 to 50 μm, preferably 1–20 μm, a BET surface area reduced to not larger than 200 m$^2$/g and a volume of pores smaller than 50 nm reduced to less than 30 percent of the total pore volume.

It was a complete surprise that silica gel with such a reduced surface area can not only be worked into dental materials in large quantities and provide them with good abrasion resistance and good polishability, but that these dental materials can also be produced with surprisingly low expansion coefficients.

Primarily, it was not expected that these advantages would result from the use of surface area-reduced silica gel because the suitability of silica gel as a filler for dental materials is still being contested in the relevant publications, DE-PS 2403211.

Surface area reduction of silica gels can be achieved by thermal or acid-catalytical treatment. The thermal treatment takes place by an extended roasting of the powders at temperatures of between 500° and 1,200° C. The temperature and the duration of roasting must be selected in such a way that the sintering process results in a sufficient surface area reduction to not more than 200 m$^2$/g (BET) and in a sufficient diminishing of pores smaller than 50 nm to less than 30 percent of the total pore volume, but the silica does not melt to a glassy mass.

In the case of acid-catalytical treatment, the starting material is boiled with acid, then washed and dried. The type of acid is not critical. All fairly strong acids are suitable. It must merely be possible to wash the acid out well and to dispel it easily in the case of a combined process. One especially advantageous acid is hydrochloric acid. Acid treatment and roasting may also be combined.

The silica gels treated in these manners exhibit a clearly reduced specific surface area but have remained essentially the same with respect to other important and favorable characteristics, for example, the refractive index. A special advantage is the fact that the grain size distribution remains approximately unchanged and thus a subsequent grinding and sifting is generally not required, in contrast to the process described in WO 81/01366.

The surface area-reduced silica gel mixes well with liquid polymerizable monomers. In this case, the mono-, di- or polyfunctional derivatives of acrylic or methacrylic acid, especially the esters, have proven themselves well for use as monomers. The filler according to the invention may, if necessary, be used together with other conventional inorganic fillers, such as quartz, amorphous silicon dioxide, glasses, ceramic or mineral fillers and/or organic unfilled or filled polymers. The inorganic filler percentage in the dental materials according to the invention should be between 10 and 80%, preferably between 30 and 80%, and most preferably between 50 and 70%, relative to the total amount of material.

The surface area-reduced silica gel may also be silanized in-order to improve the bonding wit the polymer, for example, by means of a treatment with trimethoxy (3-methacryl oxypropyl) silane. When used in dental preparations, the material is often still mixed with known organic or inorganic coloring pigments and/or opacifiers to match the natural teeth. Organic peroxides, among other substances, such as dibenzoyl peroxide, or azo compounds, such as azo-bis-iso-butyronitrile may be used as hardening catalysts in these materials. Redox systems may be used that are suitable for the cold-setting of vinyl-unsaturated monomers, such as dibenzoyl peroxide/N, N-bis-2-hydroxyethylxylidine or dibenzoyl peroxide/barbituric acid derivatives. However, hardening catalysts, which after exposure to ultraviolet or visible light trigger the polymerization, such as benzoin alkylether, benzil monoketals or aliphatic and aromatic 1,2-diketo compounds may also be used. In this case, light polymerization can be accelerated in a known manner by addition of activators, such as amines or organic phosphites.

After hardening is completed, the good characteristics of the classic "macrofiller" composites, such as low thermal expansion, high color stability and low water absorption, are combined with the good characteristics of the previously known molding substances made with amorphous silicic acid, such as high polishability and abrasion resistance, without any resulting disadvantages.

The filler according to the invention is generally suited for dental materials, not only for tooth filling preparations but also for such purposes for which materials of this type are customarily advantageously used, for example, for making and repairing crowns, bridges, veneers and similar tooth replacement parts, for making dentures or for the preparation of sealing and fastening materials.

EXAMPLE 1

Preparation of surface area-reduced silica gels by thermal treatment:

Silica gel of a mean grain size of about 2 $\mu$m, of a BET-surface of about 400 $m^2/g$ with 91 percent pore volume of pores smaller than 50 nm was roasted at a temperature of 900° C. for 18 hours. The cooled product was pressed through a 45 $\mu$m sieve and had a BET-surface of about 130 $m^2/g$ and 12 percent pore volume of pores smaller than 50 nm. The grain size distribution and the refractive index of the obtained materials were almost unchanged.

EXAMPLE 2

Silica gel having a mean grain size of about 12 $\mu$m, a BET-surface of about 400 $m^2/g$ and 93 percent pore volume of pores smaller than 50 $\mu$m was treated under the same conditions as indicated in Example 1. The obtained powder had a BET-surface of about 200 $m^2/g$ and 18 percent pore volume of pores smaller than 50 nm, but was unchanged with respect to the mean grain size of about 12 $\mu$m and a refractive index of 1.46.

EXAMPLE 3

Preparation of surface area-reduced silica gels by means of an acid-catalytic treatment:

200 g silic gel having a mean grain size of about 2 $\mu$m, a BET-surface of about 270 $m^2/g$ and 84 percent pore volume of pores smaller than 50 nm were boiled with 2.5 l concentrated HCl for two days under reflux. After filtration and repeated washing with water, drying took place at 200° C. with subsequent sifting. The obtained powder showed a reduced BET-surface of about 200 $m^2/g$ and 29 percent pore volume of pores smaller than 50nm. The grain size distribution and the refractive index were unchanged.

EXAMPLE 4

Light hardenable dental composite material:

A resinous mixture was prepared from: 285 g urethane dimethacrylate, 323 g hexane dioldimethacrylate, 380 g Bis-GMA, 4.5 g dimethoxybenzil, 2.5 g camphor quinone, 2.5 g dimethylbutyl aniline.

A paste was prepared from: 26.7 g of the above resinous mixture, 44.4 g silica gel according to Example 2 with a BET-surface reduced to 200 $m^2/g$, silanized in the conventional way; 9.7 g silica gel according to Example 1 with a BET-surface reduced to 130 $m^2/g$ silanized in the conventional way, 1.9 g pyrogenic silanized silicic acid.

The obtained material, after being colored by pigments and exposed to a commercially available halogen radiation lamp (20 sec.), exhibited a hardening depth of about 4 mm and an excellent transparency and tooth similarity. With an inorganic filler content of 68%, the material could still be polished to a high gloss and was several times more resistant to abrasion than composites of "macrofillers". It had an increased flexural modulus of 5,800 $N/mm^2$ and a linear thermal expansion coefficient of only 28 ppm/° C.

In contrast to a dental composite material made of a commercially available silica gel (see Comparative Example 1), the water absorption was reduced to 0.42 $mg/cm^2$. It was very suitable for use as tooth-filling material in the molar area.

COMPARATIVE EXAMPLE 1

Dental composite with commercially available silica gel:

A paste was prepared from: 80.7 g resinous mixture from Example 4; 44.4 g untreated silica gel of a BET-surface of 400 m²/g; mean particle size 12 μm, silanized; 9.7 g untreated silica gel, BET-surface of 400 m²/g, mean particle size 2 μm, silanized; 1.9 g pyrogenic silicic acid, silanized.

After being pigmented and completely hardened by being exposed to light, the resulting material also showed good transparency, tooth similarity, the ability to be polished to a high gloss and abrasion resistance. However, in the case of an inorganic filler content of only 41 percent by weight, the flexural modulus was only 2,700 N/mm², the linear thermal expansion coefficient was 64 ppm/° C. and water absorption was 0.81 mg/cm².

In order to obtain a paste that can be compared with the paste of the invention according to Example 4 in regard to consistency, no more than the above-indicated quantity of silica gel could be worked in.

COMPARATIVE EXAMPLE 2

The dental composite material I of the invention according to Example 4 was compared to dental composite material II according to Comparative Example 1, as well as to three commercially available dental composite materials III, IV and V. Material III is Heliosit, Vivadent; Material IV is Visio Dispers, Espe; and Material V is Adapic, Johnson & Johnson.

Material III represents a typical microfiller material (pyrogenic silica gel); material IV contains a silicic acid granulate according to WO 81/01366 as a filler; and material V contains a typical macrofiller (quartz).

|  | I | II | III | IV | V |
| --- | --- | --- | --- | --- | --- |
| Comprehensive Strength (N/mm²) | 300 | 290 | 250 | 280 | 240 |
| Flexural Strength (N/mm²) | 120 | 72 | 65 | 75 | 80 |
| Flexural Modulus (N/mm²) | 5800 | 2700 | 2600 | 3750 | 6800 |
| Thermal Expansion Coefficient (ppm/°C.) | 28 | 64 | 70 | 46 | 27 |
| Water Absorption (mg/cm²) | 0.42 | 0.81 | 0.70 | 0.25 | 0.30 |
| Polishability |  | high gloss |  | — | dull |
| Resistance to Abrasion |  | very good |  | — | low |
| Inorganic Filler Content (%) | 68 | 41 | 38 | 60 | 78 |

The above comparison shows that the dental filling material of the invention achieves the positive physical characteristics of the macrofiller composites but avoids their disadvantages. It instead exhibits the typical positive characteristics of a microfiller composite (resistance to abrasion and ability to be polished to a high gloss). In addition, its flexural strength exceeds that of the microfiller as well as of the macrofiller composites.

What is claimed is:

1. A filler for dental materials comprising a surface area-reduced silica gel, which has been prepared by roasting a silica gel of a mean grain size of about 0.5 to 50 μm at a temperature of between 500° and 1,200 ° C. and/or by acid-catalytically treating a silica gel, and which has an essentially unchanged mean grain size of about 0.5 to 50 μm, a BET surface area reduced to not larger than 200 m²/g, and a volume of pores smaller than 50 nm reduced to less than 30 percent of the total pore volume.

2. A filler according to claim 1, wherein the mean grain size is 1–20 μm.

3. A filler according to claim 1, wherein the filler is silanized.

4. A filler according to claim 2, wherein the filler is silanized.

5. A dental material which comprises a filler as defined in claim 1 and a binder resin containing polymerizable monomers and a free radical initiating agent for polymerizing said binder resin.

6. A dental material which comprises a filler according to claim 2 and a binder resin containing polymerizable monomers and a free radical initiating agent for polymerizing said binder resin.

7. A dental material which comprises a filler as defined in claim 3 and a binder resin containing polymerizable monomers and a free radical initiating agent for polymerizing said binder resin.

8. A dental material which comprises a filler as defined in claim 4 and a binder resin containing polymerizable monomers and a free radical initiating agent for polymerizing said binder resin.

9. A dental material according to claim 5, further containing one or more additional fillers selected from the group consisting of quartz, amorphous silicon dioxide, glasses, ceramic fillers, mineral fillers, organic unfilled and organic filled polymers.

10. A dental material according to claim 6, further containing one or more additional fillers selected from the group consisting of quartz, amorphous silicon dioxide, glasses, ceramic fillers, mineral fillers, organic unfilled and organic filled polymers.

11. A dental material according to claim 9 wherein the fillers are silanized.

12. A dental material according to claim 10 wherein the fillers are silanized.

13. A polymerized material for dental purposes according to claim 5.

14. A polymerized material for dental purposes according to claim 9.

15. A polymerized material for dental purposes according to claim 11.

* * * * *

UNITED STATES PATENT AND TRADEMARK OFFICE
CERTIFICATE OF CORRECTION

PATENT NO. : 4,906,446
DATED : March 6, 1990
INVENTOR(S) : Juergen ENGELBRECHT et al.

It is certified that error appears in the above-identified patent and that said Letters Patent is hereby corrected as shown below:

Title page:

<u>Foreign Application Priority Data</u>:

"July 1, 1983" should read --January 7, 1983--

Signed and Sealed this

Thirteenth Day of April, 1993

Attest:

STEPHEN G. KUNIN

*Attesting Officer*  *Acting Commissioner of Patents and Trademarks*